(12) United States Patent
Frey et al.

(10) Patent No.: US 9,045,451 B2
(45) Date of Patent: Jun. 2, 2015

(54) METHOD FOR RECOVERING DI-TRIMETHYLOLPROPANE AND TRIMETHYLOLPROPANE-ENRICHED PRODUCT STREAMS FROM THE SIDE STREAMS OF TRIMETHYLOLPROPANE PRODUCTION

(71) Applicant: Oxea GmbH, Oberhausen (DE)

(72) Inventors: Guido D. Frey, Riedstadt (DE); Thorsten Kreickmann, Oberhausen (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 0 days.

(21) Appl. No.: 14/351,205

(22) PCT Filed: Oct. 24, 2012

(86) PCT No.: PCT/EP2012/004438
§ 371 (c)(1),
(2) Date: Apr. 11, 2014

(87) PCT Pub. No.: WO2013/072006
PCT Pub. Date: May 23, 2013

(65) Prior Publication Data
US 2014/0296542 A1    Oct. 2, 2014

(30) Foreign Application Priority Data
Nov. 19, 2011 (DE) .......................... 10 2011 118 956

(51) Int. Cl.
| | |
|---|---|
| *C07C 41/42* | (2006.01) |
| *C07C 29/10* | (2006.01) |
| *C07D 319/06* | (2006.01) |
| *C07C 29/80* | (2006.01) |
| *C07C 29/90* | (2006.01) |
| *C07C 41/44* | (2006.01) |

(52) U.S. Cl.
CPC .............. *C07D 319/06* (2013.01); *C07C 29/80* (2013.01); *C07C 29/90* (2013.01); *C07C 41/42* (2013.01); *C07C 41/44* (2013.01); *C07C 29/10* (2013.01)

(58) Field of Classification Search
CPC ........ C07C 41/42; C07C 41/44; C07C 41/34; C07C 29/10; C07C 29/74; C07C 29/80; C07C 29/90

USPC .................................................. 568/680, 854
See application file for complete search history.

(56) References Cited

U.S. PATENT DOCUMENTS

| | | |
|---|---|---|
| 3,478,115 A | 11/1969 | Bronstein, Jr. et al. |
| 3,740,322 A | 6/1973 | Wada et al. |
| 3,962,347 A | 6/1976 | Herz |
| 5,210,337 A | 5/1993 | Broussard et al. |
| 5,603,835 A | 2/1997 | Cheung et al. |
| 5,948,943 A | 9/1999 | Supplee et al. |
| 6,265,623 B1 | 7/2001 | Morawietz et al. |
| 8,642,816 B2 | 2/2014 | Rauchschwalbe et al. |
| 2004/0254405 A1 | 12/2004 | Kuzuhara et al. |
| 2013/0131391 A1 | 5/2013 | Kreickmann et al. |

FOREIGN PATENT DOCUMENTS

| | | |
|---|---|---|
| DE | 2058518 A1 | 6/1971 |
| DE | 1768348 B1 | 12/1971 |
| DE | 2358297 A1 | 5/1974 |
| DE | 19840276 A1 | 3/2000 |
| DE | 10058303 A1 | 5/2002 |
| DE | 102008038021 A1 | 2/2010 |
| DE | 102010033844 A1 | 2/2012 |
| EP | 1178030 A2 | 2/2002 |
| WO | 9717313 A1 | 11/1996 |
| WO | 9701523 A1 | 1/1997 |
| WO | 9828253 A1 | 7/1998 |
| WO | 2004013074 A1 | 7/2003 |

OTHER PUBLICATIONS

International Search Report dated, Jan. 22, 2013.

*Primary Examiner* — Sikarl Witherspoon
(74) *Attorney, Agent, or Firm* — Michael W. Fenell

(57) ABSTRACT

Process for obtaining ditrimethylolpropane and trimethylolpropane-enriched product streams from the high-boiling fractions and residues which are obtained in the distillative purification of trimethylolpropane, characterized in that these high-boiling fractions and residues are combined and a polar solvent is added to produce a solution and the solution is treated at a temperature of 120 to 280° C. and at a pressure of 2 to 25 MPa with hydrogen in the presence of a solid nickel catalyst and an acidic compound. After catalytic treatment, the solution is subjected to multi-stage distillation including with a thin film evaporator with a column attachment in order to recover ditrimethylolpropane and trimethylolpropane-enriched product streams.

21 Claims, 1 Drawing Sheet

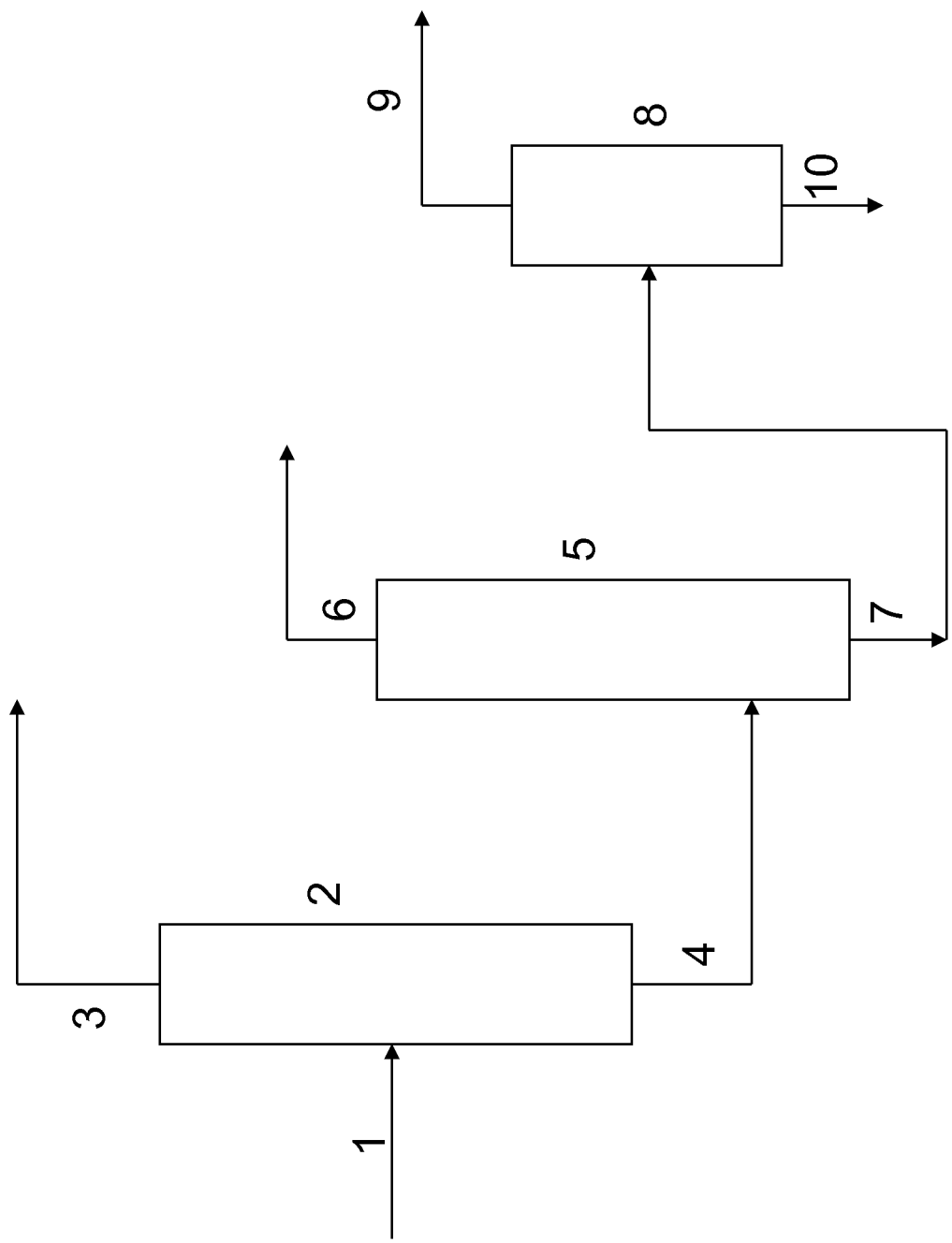

METHOD FOR RECOVERING DI-TRIMETHYLOLPROPANE AND TRIMETHYLOLPROPANE-ENRICHED PRODUCT STREAMS FROM THE SIDE STREAMS OF TRIMETHYLOLPROPANE PRODUCTION

CLAIM FOR PRIORITY

This application is a national phase application of PCT/EP2012/004438 FILED Oct. 24, 2012 which was based on application DE 10 2011 118 956.8 FILED Nov. 19, 2011. The priorities of PCT/EP2012/004438 and DE 10 2011 118 956.8 are hereby claimed and their disclosures incorporated herein by reference.

TECHNICAL FIELD

The present invention relates to a process for obtaining ditrimethylolpropane and trimethylolpropane-enriched product streams from the secondary streams of trimethylolpropane preparation.

BACKGROUND

Trimethylolpropane is a trihydric alcohol which is of significance for the production of coating materials, polyurethanes and polyesters, for example of alkyd resins. Trimethylolpropane is produced industrially by condensation reaction of n-butyraldehyde with formaldehyde according to different variants.

In what is called the hydrogenation process, at least two moles of formaldehyde are added onto one mole of n-butyraldehyde in the presence of a catalytic amount of a tertiary amine via the monomethylolbutyraldehyde intermediate to initially give dimethylolbutyraldehyde, which is then converted to trimethylolpropane in a hydrogenation step. According to the process described in WO98/28253 A1, formaldehyde is used with an up to eight-fold molar excess. The reaction mixture obtained from the aldol addition step is worked up either by distillation or by phase separation. In the distillative workup, unconverted or partly converted starting compounds are drawn off as volatile components and recycled into the reaction stage, while the bottom product is converted further. If, instead of the distillative workup, the reaction mixture is separated in a phase separator into the aqueous and organic phases, the organic phase is returned to the aldol addition and the aqueous phase is processed further. There follows a catalytic and/or thermal treatment in order to convert monomethylolbutyraldehyde to dimethylolbutyraldehyde. By-products formed are removed by distillation and the bottom product of this distillation is subsequently catalytically hydrogenated to obtain trimethylolpropane. The crude trimethylolpropane obtained is subsequently subjected to a purifying distillation. After removal of low and medium boilers, purified trimethylolpropane is obtained as an intermediate fraction, while higher-boiling condensation products within which trimethylolpropane equivalents are bound are obtained as the tailings or bottom fraction.

In addition to the hydrogenation process, trimethylolpropane is also prepared industrially by what is known as the Cannizzaro reaction. In a first reaction stage, n-butyraldehyde and formaldehyde are reacted with addition of stoichiometric amounts of a base to give dimethylolbutyraldehyde, which is subsequently reduced with excess formaldehyde to give trimethylolpropane, while one equivalent of formate is formed simultaneously. Typically, the base used is an aqueous solution of an alkali metal or alkaline earth metal compound, for example sodium hydroxide, potassium hydroxide or calcium hydroxide. Since one equivalent of alkali metal or alkaline earth metal formate is obtained as a coproduct in the Cannizzaro process, the economic viability of this process variant also depends on the marketing opportunities for this coproduct. The workup of the aqueous reaction solution obtained, which comprises trimethylolpropane, alkali metal or alkaline earth metal formate and excess base, is effected generally by extraction. After neutralization of the excess base, the aqueous solution is extracted with an organic solvent, for example with ethyl acetate. The organic phase is separated from the aqueous phase, which comprises the alkali metal or alkaline earth metal formates in dissolved form, and, after removal of the extractant, trimethylolpropane is obtained by distillation. The resulting trimethylolpropane can be subjected to further purification processes. According to U.S. Pat. No. 5,603,835, an aqueous solution is first prepared from resulting trimethylolpropane, and is extracted once again with an organic solvent, for example with methyl tert-butyl ether. Trimethylolpropane is obtained from the resulting aqueous solution with an improved colour number of less than 100 APHA units.

According to the process known from U.S. Pat. No. 5,948,943, the aqueous, crude reaction solution obtained after the Cannizzaro reaction is treated with a suitable organic solvent at such a temperature that only one liquid phase leaves the extraction vessel. In the subsequent cooling outside the extraction vessel, the aqueous phase separates from the organic phase, and trimethylolpropane can be isolated from the aqueous phase with a colour number of less than 100 APHA.

It is likewise known that the Cannizzaro reaction can be performed with an organic base, for example with a tertiary amine. According to the procedure known from WO97/17313 A1, formaldehyde is prepared with n-butyraldehyde in the presence of stoichiometric amounts of a tertiary amine, forming one equivalent of ammonium formate. Subsequently, water, excess tertiary amine and excess formaldehyde are removed from the crude mixture, and the remaining mixture is heated. This dissociates the ammonium formates to the tertiary amine and formic acid, and the tertiary amine and further volatile constituents are removed, resulting in the formation of trimethylolpropane formate. The tertiary amine removed is either recycled into the Cannizzaro stage or used as a catalyst for the transesterification of the trimethylolpropane formate in a downstream reaction with an added lower aliphatic alcohol. The trimethylolpropane released is subsequently isolated from the crude product.

Irrespective of whether the preparation of trimethylolpropane is effected by the hydrogenation process using catalytic amounts of a tertiary amine, by the Cannizzaro process with molar amounts of a tertiary amine and subsequent transesterification of the trimethylolpropane formate formed, or by the Cannizzaro process with molar amounts of alkali metal or alkaline earth metal hydroxides and the extractive removal thereof, the crude trimethylolpropane obtained is subjected to a single or multiple distillative purification, which is effected under reduced pressure due to the high boiling point. According to DE 100 58 303 A1, the distillative workup of the trimethylolpropane is combined with an ion exchanger treatment, in which case either the aldolization output or the hydrogenation output is contacted with a strongly basic ion exchanger before the distillative workup.

DE 1 768 348 B discloses reaction of two different aldehydes, for example acetaldehyde and butyraldehyde, with formaldehyde in an aqueous alkaline medium. The reaction mixture obtained is first neutralized by adding acid, freed of suspended solids and then treated with acidic and basic ion exchangers.

Distillative workup gives rise to high-boiling fractions with a higher boiling point compared to trimethylolpropane, or residues in which derivatives of trimethylolpropane are present and have formed therefrom by reaction with, for example, methanol, formaldehyde or else with a further molecule of trimethylolpropane in the upstream reactions. Among these derivatives, particularly formaldehyde-containing acetals are represented, which are characterized by the structural element —O—CH$_2$—O— and can also be regarded as formals. Among the formals, the following linear and cyclic formals of trimethylolpropane can be described structurally:

Monocyclic formal of trimethylolpropane:

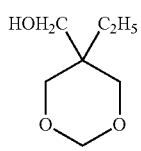

Formula I

Linear bistrimethylolpropane formal:

[C$_2$H$_5$C(CH$_2$OH)$_2$CH$_2$O]$_2$CH$_2$     Formula II

Methyl (monolinear) formal of trimethylolpropane:

C$_2$H$_5$C(CH$_2$OH)$_2$CH$_2$OCH$_2$OCH$_3$     Formula III

Methyl (bislinear) formal of trimethylolpropane:

C$_2$H$_5$C(CH$_2$OH)$_2$CH$_2$OCH$_2$OCH$_3$     Formula IV

In this context, the monocyclic formal of trimethylolpropane (I) boils at a lower temperature than trimethylolpropane itself. The methanol-derived formals (III) and (IV) have a boiling point comparable to trimethylolpropane, while the linear bistrimethylolpropane formal (formula II) is present as a high-boiling component. In addition, further linear and cyclic oxygen compounds, such as the cyclic formal of ditrimethylolpropane

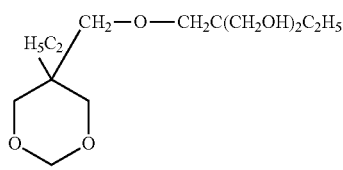

Formula V are present in the distillation residues.

Likewise present in the high-boiling fractions and residues of the distillative workup of crude trimethylolpropane are also substantial amounts of ditrimethylolpropane [CH$_2$H$_5$C(CH$_2$OH)$_2$—CH$_2$—]$_2$—O and trimethylolpropane itself. Additionally present in small amounts are low-boiling components, such as methanol or 2-ethyl-2-methyl-1,3-propanediol.

Since the high-boiling fractions and residues of the distillative workup of trimethylolpropane include considerable amounts of derivatives in which equivalents of trimethylolpropane are chemically bound, a number of processes are proposed to dissociate especially formaldehyde-containing acetals and to release trimethylolpropane, in order in this way to improve the yield of the overall trimethylolpropane preparation process. According to WO 2004/013074 A1, the high-boiling fractions and distillation residues obtained in the trimethylolpropane preparation are treated with acid, and the water content in the reaction mixture should be 20-90% by weight. It is possible either to obtain trimethylolpropane by distillation from the acid-treated product or to recycle the treated product into the hydrogenation stage of dimethylolbutyraldehyde to give trimethylolpropane.

The hydrogenating dissociation of linear or cyclic acetals in aqueous solutions in the presence of a heterogeneous hydrogenation catalyst to give the desired polyhydric alcohol is known from DE 198 40 276 A1. The process requires hydrogenation temperatures above 160° C. in order to suppress the harmful influence of formates, which may still be present particularly in the case of working by the Cannizzaro process, on the hydrogenation performance of the catalyst. The hydrogenating, catalytic dissociation can likewise be performed in the presence of an acid, for example in the presence of a lower carboxylic acid or acidic solids.

The high-boiling fractions and the residues of the distillative workup of the trimethylolpropane preparation comprise, in addition to the aforementioned formaldehyde-containing acetals, also significant amounts of ditrimethylolpropane, which is likewise of industrial significance as a valuable starting material for production of alkyd resins, plasticizers and lubricants. The prior art discloses processes for obtaining ditrimethylolpropane from these residues, and further purifying product thus obtained if required.

According to DE 2058518 A1, the ditrimethylolpropane-containing distillation residue is subjected to a steam distillation with superheated steam under reduced pressure. After removal of water, ditrimethylolpropane is obtained from the resulting aqueous distillate, and can be recrystallized if required from an organic solvent, for example acetone.

EP 1 178 030 A2 concerns a process for obtaining ditrimethylolpropane from the distillation residues of trimethylolpropane preparation. The distillation residues are treated with an acid and optionally with a hydroxylamine salt and then worked up by distillation. Ditrimethylolpropane is drawn off on a falling-film evaporator as distillate.

Since the distillative purification of ditrimethylolpropane is possible only with very great difficulty owing to the high boiling point, and there is also a risk of decomposition of the ditrimethylolpropane due to the high temperatures to be employed, the direct workup of the distillation residue by recrystallization to obtain ditrimethylolpropane is also described. DE 2358297 A1 considers the simple crystallization of an aqueous solution of the distillation residue, wherein the salt concentration in the aqueous solution is adjusted to a particular ratio in order to enable the precipitation of ditrimethylolpropane in sufficient purity. When trimethylolpropane is prepared by the Cannizzaro process, the salt content, for example the alkali metal formate content, in the distillation residue may already be sufficiently high to ensure the precipitation of ditrimethylolpropane crystals in a satisfactory manner after dissolution in water. It may be necessary to add a further salt to the aqueous solution, for example an alkali metal salt.

U.S. 2004/0254405 A1 discloses a process for recrystallizing the distillation residue using organic solvents, for example acetone or methyl ethyl ketone, which requires a particular degree of observance of the crystallization temperature, the amount of solvent and the ditrimethylolpropane content in the distillation residue. The use of a mixture of a suitable solvent and water for the isolation of ditrimethylolpropane from the distillation residues of the trimethylolpropane preparation is described in DE 10 2008 038 021 A1. An organic solvent phase and a viscous residue are initially obtained, the phases are separated and the organic solvent phase is extracted with water. The water phase is isolated and solvent residues present are removed. Ditrimethylolpropane is crystallized from the remaining water phase.

DE 10 2010 033 844 A1 likewise concerns a process for obtaining ditrimethylolpropane from the secondary streams of trimethylolpropane preparation. This involves dissolving the high-boiling fractions and residues obtained in water and catalytically hydrogenating the aqueous solution in the presence of an acidic compound to split formaldehyde-containing acetals. After removal of solids, the aqueous hydrogenated material is then contacted both with basic and with acidic ion exchangers. A trimethylolpropane-enriched product stream is distilled out of the aqueous eluate, and ditrimethylolpropane remains as the distillation residue. In order that ditrimethylolpropane is obtained in sufficient quality in the distillation residue, in the process according to DE 10 2010 033 844 A1, the treatment of the aqueous hydrogenated material both with basic and with acidic ion exchangers is absolutely necessary.

The known processes for obtaining ditrimethylolpropane from high-boiling fractions and residues which have a higher boiling point than trimethylolpropane and which are obtained in the distillative workup in the course of trimethylolpropane preparation require either complex recrystallization steps or a complex steam distillation with the subsequent removal of water from the steam distillate.

In processes in which ditrimethylolpropane is obtained as the distillation residue, ditrimethylolpropane is also not always obtained in sufficient quality to use it in a maximum number of industrial applications. In addition, before the distillation stage, purification with ion exchangers is needed to minimize the content of impurities in the distillation residue.

German patent application DE 10 2011 118 993.2, which was filed at the same time by the same applicant, concerns the distillative workup of a solution comprising high-boiling fractions and residues from trimethylolpropane preparation, which is obtained in the case of catalytic hydrogenation in the presence of acidic compounds. After solvent and low boiler removal, a trimethylolpropane-enriched tops fraction is first removed and the resulting distillation residue is distilled for removal of final runnings in a distillation unit having at least four trays. Purified ditrimethylolpropane is obtained as the top product.

The processes known to date for obtaining trimethylolpropane and ditrimethylolpropane from the secondary streams of trimethylolpropane preparation by catalytic hydrogenation of the formaldehyde-containing acetals, as described, for example, in DE 198 40 276 A1, requires compliance with a sufficiently high temperature of at least 160° C. in order to observe sufficient cleavage. According to WO 97/01523, the hydrogenation temperature can be lowered, but a high weight ratio of the catalytically active metal to the cyclic formal then has to be established in order to achieve an acceptable cleavage rate. In addition, in WO 97/01523 and DE 198 40 276 A1, all working examples are conducted with ruthenium on activated carbon catalysts in order to demonstrate the executable nature of the processes disclosed. For catalytic cleavage of the formaldehyde-containing acetals, the prior art proposes the use of costly noble metal catalysts at elevated temperature or the use thereof in a comparatively large amount, based on the formaldehyde-containing acetals.

There is therefore a need to obtain ditrimethylolpropane from such high-boiling fractions and residues in a very simple manner using inexpensive hydrogenation catalysts with such a purity required for the envisaged industrial applications. At the same time, trimethylolpropane still present in a physical mixture in these fractions and residues, and also derivatives present therein containing chemically bound trimethylolpropane units, should likewise be isolated as a trimethylolpropane-rich fraction which can be recycled back into the trimethylolpropane purification process, such that not only the recovery of pure ditrimethylolpropane but also the yield of trimethylolpropane over the entire preparation process can be improved. In this way, the high-boiling fractions and residues which are obtained in the distillative workup in the course of trimethylolpropane preparation can be utilized in a very economically viable manner.

SUMMARY OF INVENTION

The present invention therefore relates to a process for obtaining ditrimethylolpropane and trimethylolpropane-enriched product streams from the high-boiling fractions and residues which are obtained in the distillative purification of trimethylolpropane. It is characterized in that:
  (a) these high-boiling fractions and residues are combined and a polar solvent is added to produce a solution;
  (b) the solution produced according to step a) is treated at a temperature of 120 to 280° C. and at a pressure of 2 to 25 MPa with hydrogen in the presence of a solid nickel catalyst and of an acidic compound;
  (c) the solution obtained according to step b) is removed from the catalyst and further solids, if present;
  (d) the solution obtained according to step c) is separated in a first distillation unit into a tops fraction comprising the polar solvent and low boilers and into a bottoms fraction with a content of the polar solvent up to 5000 ppm by weight, based on the bottoms fraction;
  (e) the bottoms fraction obtained according to step d) is supplied to a second distillation unit with at least 5 theoretical plates and a trimethylolpropane-enriched tops fraction is drawn off and a bottoms fraction is withdrawn; and
  (f) the bottoms fraction obtained according to step e) is supplied to a third distillation unit with at least 4 theoretical plates, said unit being configured as a thin-film evaporator with column attachment, in which ditrimethylolpropane is obtained as the tops fraction and high boilers are removed as the bottoms fraction.

BRIEF DESCRIPTION OF DRAWING

The invention is described in detail below with reference to FIG. 1 which is a schematic diagram illustrating the process and apparatus of the present invention.

DETAILED DESCRIPTION

Starting materials for the process according to the invention are product streams which are obtained in the distillative purification of trimethylolpropane and have a higher boiling point than trimethylolpropane and can be referred to as high-boiling fractions.

In addition to these high-boiling components which, however, are still volatile in the distillation, the remaining distillation residue is also used in the process according to the invention. These combined product streams comprise, as main components, trimethylolpropane still present in a physical mixture, generally within a range from 5 to 30% by weight, ditrimethylolpropane, generally within a range from 10 to 35% by weight, and the linear bistrimethylolpropane formal within a range from 25 to 70% by weight, based on the overall starting material. Further identified products are 2-ethyl-2-methyl-1,3-propanediol and the monocyclic formal of trimethylolpropane, which, due to their comparatively low boiling point, are present only in small amounts of typically up to 3% by weight. Cyclic and linear formals, including the methyl (monolinear) formal of trimethylolpropane (III), the methyl (bislinear) formal of trimethylolpropane (IV) and the cyclic formal of ditrimethylolpropane (V) form the remainder of the organic components in the mixture.

Irrespective of whether trimethylolpropane is prepared by the Cannizzaro process using alkali metal or alkaline earth metal compounds or is produced by the hydrogenation process in the presence of catalytic amounts of trialkylamines, or by the Cannizzaro process using stoichiometric amounts of trialkylamines, the high-boiling fractions and the residues which are obtained in the distillative purification of trimethylolpropane by the particular preparation process are worked up in accordance with the inventive procedure. In addition, the starting mixture may also comprise alkali metal or alkaline earth metal formates, the contents of which vary as a function of the type of process employed for the preparation of trimethylolpropane.

The high-boiling fractions which have a higher boiling point than trimethylolpropane, and the residues from the distillation of trimethylolpropane, are combined, and a polar solvent is added to form a solution. A suitable polar solvent is a lower $C_1$-$C_5$ aliplatic alcohol or $C_2$-$C_{10}$ dialkyl either, for example methanol, ethanol, propanol or diethylether, or especially water. In general, a solution is prepared with a content of organic components, not including the polar solvent, of 30 to 90% by weight, preferably of 50 to 80% by weight, based on the total mass. Lower contents of organic components are inappropriate due to the high solvent content; in the case of excessively high contents, particularly at room temperature, inhomogeneities in the solution or the precipitation of solids are to be expected. It is appropriate to prepare the solution at a temperature of more than 50° C. A temperature range for the solution, especially for the aqueous solution, of 60° C. to 80° C. should preferably be established.

The solution obtained is subsequently treated at elevated temperature and elevated pressure with hydrogen in the presence of a solid nickel catalyst and of an acidic compound. The temperatures employed are in the range from 120 to 280° C., preferably 160 to 240° C., and the pressures employed are in the range from 2 to 25 MPa, preferably 6 to 22 MPa. The acidic compounds present may be protic inorganic acids, organic acids or acidic solids. Useful protic inorganic acids include phosphoric acid or sulphuric acid; useful organic acids include lower carboxylic acids such as formic acid, acetic acid, propionic acid or the isomeric butyric acids.

The amount thereof is such that the solution to be subjected to the hydrogenation has a pH in the range from 1 to 5, preferably from 2 to 4.

Due to the easy removability, however, preference is given to working with acidic solids as the acidic compound. Suitable solids of this kind are, for example, oxidic compounds such as acidic alumina, natural or silicatic substances such as mordenite, montmorillonite or acidic zeolites, for example those of the Y type, which are available in industrial amounts and are used industrially, for example, in the catalytic cracking of crude oils. The addition therefore is guided by the acidity thereof and, for every 100 parts by weight of solution, they are used generally in an amount of 0.5 to 6, preferably of 0.5 to 4.0, parts by weight, and the more acidic the solid the smaller the amounts used. This generally establishes a pH of 1 to 6, preferably of 2 to 4, in the solution.

It is also possible to use commercially available acidic ion exchangers, for example strongly acidic ion exchangers such as Amberlyst 15, Amberlite IR 120, Amberlyst DPT-1, Dowex Marathon-C, Dowex HCR, Lewatit S 100 or Nafion, or weakly acidic ion exchangers such as Amberlite ICR 86 or Lewatit CNP. The addition thereof is guided by the acidity thereof, and they are generally used in an amount of 1 to 20 and preferably of 3 to 10 parts by weight, based on 100 parts by weight of solution, and the more acidic the solid the smaller the amounts used.

The catalysts used for the hydrogenation step are solid nickel catalysts which can be removed from the reaction mixture in a simple manner, for example by simple filtration in the case of suspension hydrogenation. In the case of fixed bed catalysts too, for example in trickle or liquid phase mode, the reaction mixture can be separated easily from the fixed hydrogenation catalyst.

Nickel as the catalytically active metal can be applied to a support, generally in an amount of about 5 to 70% by weight, preferably about 10 to about 65% by weight and especially about 20 to 60% by weight, based in each case on the total weight of the catalyst. Suitable catalyst supports are all conventional support materials, for example aluminium oxide, aluminium oxide hydrates in their various manifestations, silicon dioxide, polysilicic acids (silica gels) including kieselguhr, silica zero gels, magnesium oxide, zinc oxide, zirconium oxide and activated carbon. As well as the main nickel and support material components, the catalysts may also contain additives in minor amounts, these serving, for example, to improve the hydrogenation activity thereof and/or the service life thereof and/or the selectivity thereof. Such additives are known; they include, for example, the oxides of sodium, potassium, magnesium, calcium, barium, zinc, aluminium, zirconium and chromium. They are added to the catalyst generally in a proportion totalling 0.1 to 50 parts by weight, based on 100 parts by weight of nickel.

However, it is also possible to use Raney nickel as a support-free catalyst.

The suitability of solid nickel catalysts for the hydrogenation of an aqueous formal-containing solution was not to be expected since, for example, U.S. Pat. No. 5,210,337 discloses that nickel catalysts can be damaged by the presence of formaldehyde in the hydrogenation of formals.

The hydrogenation stage is performed continuously or batchwise in the presence of the acidic compound, which is present either dissolved, for example in the case of added inorganic acids or lower organic carboxylic acids, or which is present as a solid suspended in the solution, for example over fixed bed nickel catalysts by the trickle mode or liquid phase mode, or else while stirring according to suspension hydrogenation.

In continuous mode, a catalyst hourly space velocity V/Vh, expressed in throughput volume per unit catalyst volume and unit time, of 0.1 to 1 $h^{-1}$, preferably of 0.2 to 0.5 $h^{-1}$, has been found to be appropriate. In the batchwise process regime, based on 100 parts by weight of starting solution neglecting the acidic compound, from 0.1 to 10 and preferably from 0.5 to 5 parts by weight of catalyst are used.

On completion of hydrogenation, the liquid reaction mixture is freed of solids, for example by filtration. This results in removal from solid hydrogenation catalyst and from any further solids when hydrogenation has been effected in the presence of solid acidic compounds. If the hydrogenation is performed in the presence of dissolved acidic compounds, it is advisable to neutralize with a base before the hydrogenated material is worked up further.

The liquid hydrogenated material freed of solids is then worked up by distillation. First, in a first distillation unit, the polar solvent and low boilers, especially water and methanol which has formed as a result of hydrogenation of the formaldehyde released in the acetal splitting, is removed as the tops fraction. Suitable distillation units for the removal of the polar solvent and of the low boilers are customary distillation units such as a distillation column with a reboiler which has, for example, 2 to 40 theoretical plates, a thin-film evaporator, a short-path evaporator or a vaporization vessel, which are operated typically at bottom temperatures of 100 to 180° C. and at standard pressure or appropriately under reduced pressure down to 70 hPa. The feed to the first distillation unit can be supplied at room temperature, but the feed advantageously has a temperature of 50 to 130° C., especially 80 to 120° C. The supply of the feed already having an elevated temperature can cause the polar solvent for removal to vaporize instantly and be removed via the tops fraction. The first distillation unit is operated such that the content of the polar solvent in the bottoms fraction comprising trimethylolpropane and ditrimethylolpropane is not more than 5000 ppm by weight, preferably up to 1000 ppm by weight and especially up to 500 ppm by weight, based on the mass of the bottoms fraction. Compliance with an upper limit for the solvent content in the bottoms fraction has an advantageous effect on the subsequent distillative purification. This bottoms fraction is removed from the first distillation unit and supplied to a second distillation unit. More particularly, it is possible to remove water as the polar solvent in the first distillation unit.

In the second distillation unit, the tops fraction obtained is a trimethylolpropane-enriched product stream with a content in the order of magnitude in the range from 90 to 98% by weight of trimethylolpropane, which additionally still comprises intermediate runnings and residues of the polar solvent, for example water, and low boilers. This product stream can be recycled into the purification stage of the overall process for the preparation of trimethylolpropane, appropriately into the purifying distillation stage to obtain trimethylolpropane. The tops fraction is removed in a distillation unit which has at least 5 theoretical plates, preferably at least 8 theoretical plates and especially 8 to 20 theoretical plates. In the second distillation unit, thermal stress should likewise be minimized and very short residence times should be employed. The residence time in the second distillation unit, i.e. in the entire distillation apparatus, is generally from 2 to 60 and preferably from 10 to 30 seconds. A suitable plant arrangement has been found to be a thin-film evaporator with a column attachment having the required minimum number of theoretical plates. Suitable column attachments are conventional columns with random or structured packings, preferably columns with structured packing. Such packings are commercially available, for example in the form of Montz or Sulzer packings. The thin-film evaporators for use in the process according to the invention are systems which are customary in the art and are commercially available. Less suitable apparatuses are a reboiler with column attachment or a short-path evaporator, since either the residence time in the distillation unit is too high or the separating performance is inadequate in this arrangement. The second distillation unit is generally operated at bottom temperatures of 210 to 280° C. and a pressure of 2 to 10 hPa. The bottoms fraction from the second distillation unit is then supplied to a third distillation unit.

The third distillation unit can also be considered as a tailings removal unit and serves to obtain ditrimethylolpropane in adequate quality. Ditrimethylolpropane is removed as the tops fraction, and low boilers are withdrawn from the third distillation unit as the bottoms fraction. In order to obtain ditrimethylolpropane in adequate quality, the third distillation unit has to have at least 4 theoretical plates and especially 4 to 20 theoretical plates. In the third distillation column, thermal stress should likewise be minimized, and minimum residence times should be employed. The residence time of the tops fraction in the third distillation unit is generally from 1 to 30 and preferably from 5 to 20 seconds. The plant arrangement used is a thin-film evaporator with a column attachment having the required minimum number of theoretical plates. Suitable column attachments are conventional columns with random or structured packings, preferably columns with structured packing. Such packings are commercially available, for example in the form of Montz or Sulzer packings. The thin-film evaporators for use in the process according to the invention are systems which are customary in the art and are commercially available. Unsuitable apparatuses are a reboiler with column attachment or a short-path evaporator, since the residence time of the top product in the distillation unit is either too high or the separating performance is inadequate in this arrangement. The third distillation unit is generally operated at bottom temperatures of 240 to 280° C. and a pressure of 0.2 to 5 hPa. A maximum bottom temperature of 280° C. should not be exceeded in order to avoid excessive decomposition of ditrimethylolpropane.

The ditrimethylolpropane removed via the tops fraction is obtained in a quality sufficient for industrial applications, and it is possible to obtain product of value contents determined by gas chromatography of more than 98% by weight. It is also possible to attain sulphate ash contents determined to DIN 51575, modified with addition of sulphuric acid after the burning and before the annealing of the sample, in the ditrimethylolpropane purified by distillation of below 100 ppm and generally between 15 and 80 ppm.

In a further configuration of the process according to the invention, before the distillative workup of the hydrogenated material which has been freed of solids, there may be an optional treatment with an ion exchanger, for example either only with a basic or acidic ion exchanger or with a combination in any sequence. Customary temperatures in the range from 1 to 100° C., preferably in the range from 20 to 70° C., and standard pressure are employed.

If the hydrogenation was effected in the presence of dissolved inorganic acids or lower organic carboxylic acids, the solution is neutralized by addition of base after removal of the solid hydrogenation catalyst. In this case too, there may follow treatment with an ion exchanger, specifically at customary temperatures in the range from 1 to 100° C., preferably in the range from 20 to 70° C., and at standard pressure. The ion exchanger treatment removes not only the salts formed after addition of base but additionally further impurities.

The basic ion exchangers include those which contain primary, secondary, tertiary or quaternary amino groups. Particular significance has been gained by polystyrene-based ion exchangers which contain tertiary amino groups or quaternary amino groups in the base form. Examples of weakly to strongly basic ion exchangers are Amberlit IR 45, Dowex 4 or Dowex Marathon-A. Particular industrial significance has been gained by macroreticular types such as Amberlyst A21, Lewatit MP62, Lewatit MP64, Imac A20, Zerolit G, Amberlit IRA93 or Amberlyst A26.

Weakly or strongly acidic ion exchangers contain, for example, the carboxylate group or the sulpho group, which are bonded to a polymer matrix based on styrene-divinylbenzene copolymers. The carboxylate group can be derived, for example, from aromatic carboxylic acids or aliphatic carboxylic acids, and the sulpho group from aromatic or aliphatic sulphonic acids. A strongly acidic ion exchanger is, for example, Amberlyst 15, Amberlyst DPT-1 or Dowex Marathon-C.

The solution is contacted with the ion exchanger in a suitable reactor. The ion exchanger may be arranged, for example, as a fixed bed in a tubular reactor, through which the solution flows. The fixed bed volume and the size of the ion exchanger particles can be varied within wide ranges and thus adjusted to the selected reaction conditions and the process circumstances, such as the desired flow rate. It has been found to be useful to observe space velocities in the range from 1 to 10, especially from 5 to 8 ($V_{solution}/V_{ion\ exchanger} \cdot h$]). These are guide parameters which should appropriately be selected.

In another embodiment of the inventive procedure, the ion exchanger, which in this case may be very finely divided, is suspended in the solution. It is appropriate to keep the suspension in constant motion, for example by stirring or introducing a gas, for example air or nitrogen, in order to achieve intimate contact between the liquid phase and the ion exchanger. The mass ratio of liquid phase to ion exchanger can be adjusted substantially freely and hence in accordance with the individual requirements. It has been found to be useful, for every 100 parts by weight of solution, to use 1 to 10 and preferably 3 to 8 parts by weight of ion exchanger. For the performance of this process variant, stirred tanks or autoclaves, for example, are suitable.

In this procedure, the ion exchanger, however, is subject to mechanical stress and, for the mixing of liquid phase with the ion exchanger, the conditions should be adjusted such that abrasion at the surface of the particles or even mechanical damage to the particles is prevented.

The solution can be recirculated in order to complete the removal of impurities by multiple treatment of the liquid phase. It is equally possible to perform the adsorption in several stages; either a batchwise or continuous reaction regime is possible. The optional ion exchanger treatment is particularly suitable in the workup of an aqueous hydrogenated material.

After the ion exchanger treatment of the liquid hydrogenated material, the resulting eluate is worked up by distillation as described above in the three-stage arrangement of distillation units. To obtain ditrimethylolpropane in adequate quality, the optional treatment of the liquid hydrogenated material with the ion exchanger is not absolutely necessary. However, this additional purification step may be found to be advantageous when the secondary streams of the trimethylolpropane preparation for workup are laden with a high salt burden. Salt impurities can be removed by the treatment with the ion exchanger. They are found to be troublesome since they can promote the decomposition of ditrimethylolpropane in the subsequent distillative workup due to the comparatively high bottom temperatures. Volatile cleavage products released have an adverse effect on the pressure conditions to be established in the distillation, and so not only the yield of ditrimethylolpropane but also the quality can suffer.

In a further configuration of the process according to the invention, the liquid hydrogenated material is obligatorily treated with an ion exchanger after removal of acidic solids or after neutralization with bases. The liquid hydrogenated material is contacted either only with a basic or acidic ion exchanger or with a combination in any sequence. The now obligatory ion exchanger treatment is effected as in the optional mode of operation described above.

The present invention therefore likewise consists in a process for obtaining ditrimethylolpropane and trimethylolpropane-enriched product streams from the high-boiling fractions and residues which are obtained in the distillative purification of trimethylolpropane, characterized in that:
a) these high-boiling fractions and residues are combined and a polar solvent is added to produce a solution;
b) the solution produced according to step a) is treated at a temperature of 120 to 280° C., preferably of 160 to 240° C., and at a pressure of 2 to 25 MPa, preferably of 6 to 22 MPa, with hydrogen in the presence of a solid nickel catalyst and of an acidic compound;
c) the solution obtained according to step b) is removed from the catalyst and further solids, if present;
d) the solution obtained according to step c) is treated with an ion exchanger,
e) the polar solvent and low boilers are removed from the eluate obtained after step d) in a distillation unit to obtain a bottoms fraction having a content of the polar solvent up to 5000 ppm by weight, based on the bottoms fraction, and
f) a trimethylolpropane-enriched product stream is distilled at elevated temperature and reduced pressure out of the bottoms fraction obtained after step e), leaving ditrimethylolpropane as distillation residue.

The eluate obtained after ion exchanger treatment which is effected either only with a basic or only with an acidic ion exchanger or with a combination in any sequence, is likewise worked up by distillation. First of all, the polar solvents and low boilers, especially water and methanol which has formed as a result of hydrogenation of the formaldehyde released in the acetal splitting are removed as first runnings. Suitable distillation units for the removal of the polar solvent and of the low boilers are customary batchwise or continuous distillation units, such as a distillation column having, for example, 2 to 40 theoretical plates, with a reboiler, a thin-film evaporator, a short-path evaporator or a vaporization vessel, which are operated typically at bottom temperatures of 100 to 160° C. and at standard pressure or appropriately under reduced pressure down to 70 hPa. The feed to the distillation unit can be supplied at room temperature, but the feed advantageously has a temperature of 50 to 130° C., especially 80 to 120° C. The supply of the feed already having an elevated temperature can cause the polar solvent for removal to vaporize instantly and be removed via the tops fraction. The distillation unit is operated such that the content of the polar solvent in the bottoms fraction comprising trimethylolpropane and ditrimethylolpropane is not more than 5000 ppm by weight, preferably up to 1000 ppm by weight and especially up to 500 ppm by weight, based on the mass of the bottoms fraction. Compliance with an upper limit for the solvent content in the bottoms fraction has an advantageous effect on the subsequent distillative purification. More particularly, it is possible to remove water as the polar solvent in the first runnings fraction.

After removal of the predominant amount of the polar solvent and of the low boilers, the bottom temperature is increased to 180 to 230° C. and the pressure is simultaneously lowered down to 2 hPa. The top product obtained is a trimethylolpropane-enriched product stream having a content in the order of magnitude in the range around 90 to 96% trimethylolpropane. After predominant removal of the trimethylolpropane, the bottom temperature is raised up to 260° C. in order to drive out the last fractions of volatile components. Ditrimethylolpropane remains in the distillation residue as a pale yellowish liquid which generally has a product of value content determined by gas chromatography in the range of 94-98% by weight and has sufficient quality for industrial applications. After cooling to room temperature, a virtually white powder is obtained.

The sulphate ash content determined to DIN 51575, modified with addition of sulphuric acid after the burning and before the annealing of the sample, can be distinctly reduced and is generally within a range from 200 to 300 ppm.

The trimethylolpropane-enriched product stream drawn off is recycled into the purification stage of the overall process for the preparation of trimethylolpropane, appropriately into the purifying distillation stage to obtain trimethylolpropane. The temperature and pressure figures are guide values which can be optimized in a routine manner. In order to avoid the decomposition of ditrimethylolpropane in the distillation bottoms, the bottom temperature, however, should not be increased too far above the guide values specified.

FIG. 1 shows a block diagram for the three-stage distillative treatment of the liquid hydrogenated material which has been freed of solids, if appropriate after the treatment with an ion exchanger, in accordance with one embodiment of the process according to the invention. The preferably heated solution comprising trimethylolpropane and ditrimethylolpropane supplied via line (1) is introduced to a first distillation unit (2), in which polar solvent and low boilers, for example water and methanol, are removed at the top via line (3). Via the bottom of the first distillation unit (2), with line (4), the bottoms fraction is removed, in which the content of the polar solvent is not more than 5000 ppm by weight, based on the mass of the bottoms fraction. The first distillation unit (2) is a customary column with, for example, 2 to 40 theoretical plates. The bottoms fraction from the first distillation unit (2) is introduced to a second distillation unit (5) which has at least 5 theoretical plates and which is configured, for example, as a thin-film evaporator with column attachment. Via line (6), the tops fraction comprising predominantly trimethylolpropane, intermediate runnings and residues of the polar solvent and low boilers is withdrawn and recycled into the process for preparing trimethylolpropane. The bottoms fraction from the second distillation unit (5) is removed via line (7) and introduced to the third distillation unit (8). This third distillation unit or else tailings removal unit has at least 4, for example 5, theoretical plates and is configured as a thin-film evaporator with column attachment. Via line (9), ditrimethylolpropane is removed as the tops fraction in adequate quality, while high boilers are discharged from the process via line (10).

The process according to the invention permits the economic utilization of high-boiling fractions and residues which are obtained in the distillative purification of trimethylolpropane. The recycling of the trimethylolpropane-rich product streams obtained therefrom in the overall preparation process allows the plant efficiency and the yield of trimethylolpropane to be improved compared to a process regime in which the high-boiling fractions and residues from the trimethylolpropane distillation are not worked up and not recycled. At the same time, the inventive procedure gives rise to ditrimethylolpropane in a quality sufficient for industrial applications.

The examples which follow describe the process according to the invention in detail. It is of course not restricted to the embodiment described.

EXAMPLES

Example 1

For the inventive workup of the high-boiling fractions and residues from the distillative purification of trimethylolpropane, a mixture was used which had the following composition determined by gas chromatography (%):

| | |
|---|---|
| First runnings | — |
| Monocyclic formal (I) | 0.1 |
| Trimethylolpropane | 19.0 |
| Intermediate fraction I | 2.6 |
| Ditrimethylolpropane | 20.5 |
| Intermediate fraction II | 16.5 |
| Linear bistrimethylolpropane formal (II) | 33.2 |
| High boilers | 8.1 |

Water at 60° C. was added to the organic residue to produce a homogeneous aqueous solution with a content of 60% by weight of dissolved organic residue. To 100 parts by weight of aqueous solution were added 5 parts by weight of a commercial nickel catalyst, PRICAT Ni52/35 from Johnson Matthey, with a nickel loading of 52% by weight, and 2.7 parts by weight of dilute sulphuric acid (5%). The resulting suspension was subsequently treated with hydrogen in a 1 liter autoclave under the following conditions:

TABLE 1

Hydrogenation of an aqueous solution of residues from the trimethylolpropane distillation over a nickel catalyst in the presence of 5% sulphuric acid

| Reaction conditions | Experiment 1 | Experiment 2 | Experiment 3 |
|---|---|---|---|
| Temperature (° C.) | 200 | 200 | 220 |
| Pressure (MPa) | 20 | 20 | 20 |
| Reaction time (h) | 5 | 10 | 5 |
| Composition determined by gas chromatography (%; organic content, anhydrous): | | | |
| First runnings | 3.6 | 5.5 | 11.9 |
| Monocycl. formal (I) | 4.7 | 4.7 | 4.9 |
| Trimethylolpropane | 66.9 | 67.9 | 62.8 |
| Intermediate fraction I | 2.0 | 2.1 | 2.3 |
| Ditrimethylolpropane | 20.0 | 19.1 | 17.2 |
| Intermediate fraction II | 0.5 | 0.2 | 0.2 |
| Linear bistrimethylolpropane formal (II) | 1.8 | 0.4 | 0.4 |
| High boilers | 0.5 | 0.1 | 0.3 |

Example 2

For the inventive workup of the high-boiling fractions and residues from the distillative purification of trimethylolpropane, a mixture was used which had the following composition determined by gas chromatography (%):

| | |
|---|---|
| First runnings | 6.7 |
| Monocyclic formal (I) | — |
| Trimethylolpropane | 19.0 |
| Intermediate fraction I | 8.3 |
| Ditrimethylolpropane | 12.9 |
| Intermediate fraction II | 14.1 |
| Linear bistrimethylolpropane formal (II) | 34.9 |
| High boilers | 4.1 |

Water at 60° C. was added to the organic residue to produce a homogeneous aqueous solution with a content of 60% by weight of dissolved organic residue. To 100 parts by weight of aqueous solution were added 1.5 part by weight of a commercial nickel catalyst, PRICAT Ni52/35 from Johnson Matthey, in powder form with a metal loading of 52% by weight, and 3 parts by weight of an acidic commercial Y-type zeolite. The resulting suspension was subsequently treated with hydrogen in a 1 liter autoclave under the following conditions:

TABLE 2

Hydrogenation of an aqueous solution of
residues from trimethylolpropane distillation over a
nickel catalyst in the presence of Y-type zeolite
(Zeolyst CBV 600)

| Reaction conditions | Experiment 4 | Experiment 5 | Experiment 6 |
|---|---|---|---|
| Temperature (° C.) | 180 | 200 | 210 |
| Pressure (MPa) | 7 | 8 | 8 |
| Reaction time (h) | 7 | 6 | 8 |
| Composition determined by gas chromatography (%; organic content, anhydrous): | | | |
| First runnings | 13.8 | 9.8 | 31.9 |
| Monocycl. formal (I) | 19.3 | 10.8 | 6.6 |
| Trimethylolpropane | 51.8 | 63.2 | 45.6 |
| Intermediate fraction I | 4.7 | 2.8 | 3.8 |
| Ditrimethylolpropane | 10.2 | 13.1 | 11.6 |
| Intermediate fraction II | 0.1 | 0.1 | 0.2 |
| Linear bistrimethylolpropane formal (II) | 0.1 | 0.2 | 0.1 |
| High boilers | — | — | 0.2 |

Example 3

For the distillative workup of the hydrogenated material obtained after filtration of the catalyst and of the acidic zeolite according to Example 2, with the conditions of Experiment 5, an aqueous solution which contained 40% by weight of water and 60% by weight of organic components was used with the composition (%) of the hydrogenated organic component determined by gas chromatography and specified in Experiment 5.

Example 3a

Removal of Water and First Runnings

In a first distillation, in a 20-tray column with reboiler, at a bottom temperature of 96° C. and a pressure of 73 hPa, water and low boilers were removed as distillate. The resulting distillation bottoms contained about 800 ppm by weight of water and had the following composition determined by gas chromatography (%):

| | |
|---|---|
| First runnings | 0.6 |
| Monocyclic formal (I) | 0.1 |
| Trimethylolpropane | 72.0 |
| Intermediate fraction I | 0.8 |
| Ditrimethylolpropane | 26.0 |
| Intermediate fraction II | 0.1 |
| Linear bistrimethylolpropaneformal (II) | 0.1 |
| High boilers | 0.3 |

Example 3b

Removal of Trimethylolpropane-Enriched Product Streams

The bottom product from the first distillation according to Example 3a was used for the second distillation. The second distillation was configured such that intermediate fractions in the distillation bottoms were depleted as far as possible. Table 3 compiles different embodiments for the second distillation. The gas chromatography analysis represents the composition (%) of the input and the composition of the distillation bottoms.

TABLE 3

Removal of trimethylolpropane-enriched product streams from the
distillation bottoms according to Example 3a;
gas chromatography analysis of the bottom products

| | | Input | 3b (1) Thin-film evaporator with column having random packings | 3b (2) Thin-film evaporator with column having structured packings | 3b (3) Only column with structured packing with reboiler |
|---|---|---|---|---|---|
| Temperatures | | | | | |
| Top | [° C.] | | 160 | 163 | 165 |
| Side | [° C.] | | — | 242 | 190 |
| Jacket/bottom | [° C.] | | 270 | 265 | 269 |
| Column top | [hPa] | | 5 | 5 | 4 |
| Pressure difference | [hPa] | | 29 | 11 | 17 |
| Reflux ratio | | | ⅓ | none | none |
| Tops removal | [%] | | 76 | 75.3 | 77 |
| Bottoms removal | [%] | | 24 | 24.7 | 23 |
| Number of plates | | | 11 | 15 | 15 |
| Residence time | [s] | | 10-30 | 10-30 | 3-5 hours |
| Gas chromatography composition (%): | | | | | |
| First runnings | | 0.6 | 0.1 | 0.1 | 0.1 |
| Monocyclic formal (I) | | 0.1 | 0.0 | 0.0 | 0.0 |
| Trimethylolpropane | | 72.0 | 0.1 | 0.3 | 0.1 |
| Intermediate fraction I | | 0.8 | 1.5 | 0.4 | 0.9 |
| Ditrimethylolpropane | | 26.0 | 97.3 | 98.1 | 97.5 |
| Intermediate fraction II | | 0.1 | 0.1 | 0.1 | 0.1 |
| Linear bistrimethylol-propane formal (II) | | 0.1 | 0.1 | 0.0 | 0.1 |
| High boilers | | 0.3 | 0.8 | 1.0 | 1.2 |

As Example 3b (2) shows, the use of a column with structured packing, for example a column with a diameter of 40 mm equipped with a Montz packing, allows the intermediate fraction I in the bottoms to be depleted. In the case of Example 3b (3), comparatively high residence times have to be employed, such that decompositions form volatile compounds at the high distillation temperatures and a comparatively high pressure difference is observed during the distillation compared to Example 3b (2), which works with the same column type. Nevertheless, in this configuration of the second distillation too, a bottom product with a ditrimethylolpropane content of 97.5% is obtained.

The use of a column with structured packing having a higher number of plates is, however, preferable to a column with random packing.

Example 3c

Tailings Removal

The bottom product obtained according to Example 3b (3) was used for the third distillation for tailings removal. The desired ditrimethylolpropane was obtained as the top product in adequate quality. The distillation conditions and the gas chromatography analysis (%) of the distillate are reported in Table 4.

TABLE 4

Tailings removal from the bottom product according to Example 3b (3), gas chromatography analysis (%) of the distillate

|  |  | Input Example 3b (3) | 3c (4) Thin-film evaporator with column having structured packings | 3c (5) comparative Only column with random packing with reboiler | 3c (6) Thin-film evaporator with column having structured packings |
|---|---|---|---|---|---|
| Temperatures |  |  |  |  |  |
| Top | [° C.] |  | 222 | 235 | 135 |
| Side | [° C.] |  | 230 | 240 | 160 |
| Bottom | [° C.] |  | 265 | 290-70 | 265 |
| Column top | [hPa] |  | 3 | 5 | 0.3 |
| Pressure difference | [hPa] |  | 10 | 30-35 | — |
| Reflux ratio |  |  | none | none | none |
| Tops removal | [%] |  | 90.1 | 76.2 | 95.4 |
| Bottoms removal | [%] |  | 9.9 | 23.8 | 4.6 |
| Number of plates |  |  | 15 | 15 | 15 |
| Residence time | [s] |  | 5-8 | 3-5 hours | 5-9 |
| Gas chromatography composition (%): |  |  |  |  |  |
| First runnings |  | 0.1 | 0.0 | 11.5 | 0.0 |
| Monocyclic formal (I) |  | 0.0 | 0.0 | 0.0 | 0.0 |
| Trimethylolpropane |  | 0.1 | 0.6 | 14.8 | 0.5 |
| Intermediate fraction I |  | 0.9 | 0.1 | 2.2 | 0.1 |
| Ditrimethylolpropane |  | 97.5 | 98.6 | 70.7 | 98.5 |
| Intermediate fraction II |  | 0.1 | 0.5 | 0.3 | 0.7 |
| Linear bistrimethylolpropane formal (II) |  | 0.1 | 0.0 | 0.1 | 0.1 |
| High boilers |  | 1.2 | 0.2 | 0.4 | 0.1 |
| DIN 51575 ash value, modified |  |  | <50 ppm | — | <50 ppm |
| ASTM D1544 Gardner colour number |  | >6 | 1 | 1 | 1 |

As the comparison of Examples 3c (4) and 3c (6) with Comparative Example 3c (5) shows, the use of a thin-film evaporator with a column attachment is required, to obtain ditrimethylolpropane as the top product in adequate quality. A distillation unit composed of a reboiler with column attachment is unsuitable for the tailings removal since, in the case of this arrangement, due to the high temperatures and long residence times, there is increased decomposition, indicated by clear formation of first runnings and decrease in the ditrimethylolpropane content.

Example 4

The aqueous solution obtained according to Example 2, hydrogenation conditions according to Experiment 5, was pumped at a temperature of 20° C. first over a bed filled with the basic ion exchanger Dowex Marathon-A at a space velocity V/Vh of 5 h$^{-1}$, and then over a bed filled with the acidic ion exchanger Dowex Marathon-C, likewise with a space velocity V/Vh of 5 h$^{-1}$. The resulting eluate was subsequently worked up in a continuous distillation apparatus. In this apparatus, the bottom product of the first distillation was used as the starting material for the second distillation. For the distillations, a laboratory column filled with random packings in the form of Raschig rings and having 8 theoretical plates was used in the first distillation, and one having 4 theoretical plates in the second distillation. The results of the continuous distillative workup of the aqueous eluate are reproduced in Table 5.

TABLE 5

Continuous distillative workup of the aqueous solution of residues from trimethylolpropane preparation after hydrogenation and treatment with ion exchangers

|  |  | Input | Distillation 1 8 plates Tops | Bottoms Distillation 1 | Distillation 2 4 plates Bottoms Distillation 2 |
|---|---|---|---|---|---|
| Pressure | [hPa] |  | 10 |  | 2 |
| Top | [° C.] |  | 156-198 |  | 204 |
| Bottom | [° C.] |  | 185-240 |  | 261 |
| Reflux ratio |  |  | None |  | None |
| Amount | [g/h]* | 1711.5 | 1221.6 | 486.6 | 432.6 |
| Gas chromatography analysis (%): |  |  |  |  |  |
| First runnings |  | 1.1 | 2.1 | 0 | 0 |
| Monocyclic formal (I) |  | 8.2 | 11.6 | 0 | 0 |
| Trimethylolpropane |  | 61.9 | 83.4 | 0.8 | 0.1 |
| Intermediate fraction I |  | 3.5 | 2.8 | 8.7 | 0.9 |
| Ditrimethylolpropane |  | 25.0 | 0 | 87.7 | 96.7 |
| Intermediate fraction II |  | 0.1 | 0.1 | 0.5 | 0 |
| Linear bistrimethylolpropane formal (II) |  | 0 | 0 | 0 | 0 |
| High boilers |  | 0.2 | 0 | 2.3 | 2.3 |

*Mass balance [g/h]: First distillation: Input: 1711.5 Bottoms: 486.6 Tops: 1221.6 Distillation loss: 3.3 Second distillation: Input: 486.6 Bottoms: 432.6 Tops/distillation loss: 54.0

The resulting distillation residue of ditrimethylolpropane was subsequently analysed for the sulphate ash content to DIN 51575, modified with addition of sulphuric acid. The ditrimethylolpropane residues obtained by the process according to the invention had a sulphate ash content in the range from 200 to 300 ppm.

Example 5 (Comparative Example with Respect to Example 4)

The hydrogenation of the aqueous solution of residues from the trimethylolpropane distillation was conducted like Example 2, with hydrogenation conditions according to Experiment 5. In contrast to the inventive mode of operation, however, solids removal was followed by fractional distillation of the aqueous solution without treatment with the acidic and basic ion exchangers. In the resulting ditrimethylolpropane residues, the sulphate ash content was likewise determined by the modified process to DIN 51575. Without the treatment of the aqueous hydrogenation output with ion exchangers, sulphate ash contents of 1000 to 1500 ppm were found.

As Inventive Example 4 demonstrates, it is possible to distillatively remove a trimethylolpropane-rich product stream from the high-boiling fractions and residues which are obtained in the distillative purification of trimethylolpropane, while ditrimethylolpropane with a reduced sulphate ash content which remains at the same time in the distillation residue has a sufficient quality for industrial applications.

The invention claimed is:
1. Process for obtaining ditrimethylolpropane and trimethylolpropane-enriched product streams from the high-boiling fractions and residues which are obtained in the distillative purification of trimethylolpropane, characterized in that:
   (a) these high-boiling fractions and residues are combined and a polar solvent is added to produce a solution;

(b) the solution produced according to step a) is treated at a temperature of 120 to 280° C. and at a pressure of 2 to 25 MPa with hydrogen in the presence of a solid nickel catalyst and of an acidic compound;

(c) the solution obtained according to step b) is removed from the catalyst and further solids, if present;

(d) the solution obtained according to step c) is separated in a first distillation unit into a tops fraction comprising the polar solvent and low boilers and into a bottoms fraction with a content of the polar solvent up to 5000 ppm by weight, based on the bottoms fraction;

(e) the bottoms fraction obtained according to step d) is supplied to a second distillation unit with at least 5 theoretical plates and a trimethylolpropane-enriched tops fraction is drawn off and a bottoms fraction is withdrawn; and (f) the bottoms fraction obtained according to step e) is supplied to a third distillation unit with at least 4 theoretical plates, said unit being configured as a thin-film evaporator with column attachment in which ditrimethylolpropane is obtained as the tops fraction and high boilers are removed as the bottoms fraction.

2. Process according to claim 1, characterized in that the solution prepared according to step a) is treated with hydrogen at a temperature of 160 to 240° C. and at a pressure of 6 to 22 MPa.

3. Process according to claim 1, characterized in that the bottoms fraction obtained according to step d) has a content of the polar solvent up to 1000 ppm by weight and especially up to 500 ppm by weight, based on the bottoms fraction.

4. Process according to claim 1, characterized in that the second distillation unit has at least 8 theoretical plates.

5. Process according to claim 1, characterized in that the second distillation unit is configured as a thin-film evaporator with column attachment.

6. Process according to claim 5, characterized in that the column attachment is configured as a column with random packing or column with structured packing.

7. Process according to claim 1, characterized in that the second distillation unit is operated at a temperature of 210 to 280° C. and at a pressure of 2 to 10 hPa.

8. Process according to claim 1, characterized in that the second distillation unit is operated with a residence time of 2 to 60 seconds.

9. Process according to claim 1, characterized in that the third distillation unit has 4 to 20 theoretical plates.

10. Process according to claim 1, characterized in that the column attachment is configured as a column with random packing or column with structured packing.

11. Process according to claim 1, characterized in that the third distillation unit is operated at a temperature of 240 to 280° C. and at a pressure of 0.2 to 5 hPa.

12. Process according to claim 1, characterized in that the residence time of the tops fraction in the third distillation unit is 1 to 30 seconds.

13. Process according to claim 1, characterized in that the solution obtained according to step c), after step c) and before step d), is treated with an ion exchanger.

14. Process according to claim 13, characterized in that the solution obtained after step c) is treated both with a basic and an acidic ion exchanger in any sequence.

15. Process according to claim 1, characterized in that the polar solvent used is a $C_1$-$C_5$ aliphatic alcohol, a $C_2$-$C_{10}$ dialkyl ether or water.

16. Process for obtaining ditrimethylolpropane and trimethylolpropane-enriched product streams from the high-boiling fractions and residues which are obtained in the distillative purification of trimethylolpropane, characterized in that:

a) these high-boiling fractions and residues are combined and a polar solvent is added to produce a solution;

b) the solution produced according to step a) is treated at a temperature of 120 to 280° C. and at a pressure of 2 to 25 MPa with hydrogen in the presence of a solid nickel catalyst and of an acidic compound;

c) the solution obtained according to step b) is removed from the catalyst and further solids, if present;

d) the solution obtained according to step c) is treated with an ion exchanger, e) the polar solvent and low boilers are removed from the eluate obtained after step d) in a distillation unit to obtain a bottoms fraction having a content of the polar solvent up to a maximum of 5000 ppm by weight, based on the bottoms fraction, and f) a trimethylolpropane-enriched product stream is distilled at elevated temperature and reduced pressure out of the bottoms fraction obtained after step e), leaving ditrimethylolpropane as distillation residue.

17. Process according to claim 16, characterized in that the solution prepared according to step a) is treated with hydrogen at a temperature of 160 to 240° C. and a pressure of 6 to 22 MPa.

18. Process according to claim 16, characterized in that a trimethylolpropane-enriched product stream is distilled at a temperature of up to 260° C. out of the distillation residue in step f).

19. Process according to claim 16, characterized in that the bottoms fraction obtained according to step e) has a content of the polar solvent up to 1000 ppm by weight and especially up to 500 ppm by weight, based on the bottoms fraction.

20. Process according to claim 16, characterized in that the ion exchanger treatment according to step d) is effected both with a basic and with an acidic ion exchanger in any sequence.

21. Process according to claim 16, characterized in that the polar solvent used is a $C_1$-$C_5$ aliphatic alcohol, a $C_2$-$C_{10}$ dialkyl ether or water.

* * * * *